US007979105B2

(12) United States Patent
Kipke et al.

(10) Patent No.: US 7,979,105 B2
(45) Date of Patent: *Jul. 12, 2011

(54) INTRACRANIAL NEURAL INTERFACE SYSTEM

(75) Inventors: Daryl R. Kipke, Dexter, MI (US);
Justin C. Williams, Madison, WI (US);
Jamille Hetke, Brooklyn, MI (US);
Jaimie Henderson, Stanford, CA (US);
P. Charles Garell, Madison, WI (US)

(73) Assignees: The Regents of the University of Michigan, Ann Arbor, MI (US);
Wisconsin Alumni Research Foundation, Madison, WI (US)

( * ) Notice: Subject to any disclaimer, the term of this patent is extended or adjusted under 35 U.S.C. 154(b) by 38 days.

This patent is subject to a terminal disclaimer.

(21) Appl. No.: 12/483,696

(22) Filed: Jun. 12, 2009

(65) Prior Publication Data
US 2009/0253977 A1 Oct. 8, 2009

Related U.S. Application Data

(63) Continuation of application No. 10/970,268, filed on Oct. 21, 2004, now Pat. No. 7,548,775.

(60) Provisional application No. 60/513,035, filed on Oct. 21, 2003.

(51) Int. Cl.
*A61B 5/04* (2006.01)
*A61N 1/05* (2006.01)
(52) U.S. Cl. ........................ 600/378; 607/116
(58) Field of Classification Search .............. 600/378; 607/116
See application file for complete search history.

(56) References Cited

U.S. PATENT DOCUMENTS

| 3,847,687 A | 11/1974 | Davidsohn et al. |
| 3,921,916 A | 11/1975 | Bassous |
| 4,461,304 A | 7/1984 | Kuperstein |
| 5,207,709 A | 5/1993 | Picha |
| 5,215,088 A | 6/1993 | Normann et al. |
| 5,308,442 A | 5/1994 | Taub et al. |
| 5,385,635 A | 1/1995 | O'Neill |
| 5,585,827 A | 12/1996 | Murakami |
| 5,588,597 A | 12/1996 | Reinecke et al. |
| 5,843,150 A | 12/1998 | Dreessen et al. |
| 5,927,277 A | 7/1999 | Baudino et al. |
| 5,938,694 A | 8/1999 | Jaraczewski et al. |

(Continued)

FOREIGN PATENT DOCUMENTS
WO WO-01/12115 A1 2/2001
(Continued)

OTHER PUBLICATIONS

PCT International Search Report of PCT/US2004/035030, filed Oct. 21, 2004 (4 pages).

(Continued)

*Primary Examiner* — Lee S Cohen
(74) *Attorney, Agent, or Firm* — Rader, Fishman & Grauer PLLC; James F. Kamp

(57) ABSTRACT

In some preferred embodiments, without limitation, the present invention comprises an implantable, intracranial neural interface node which is an integrated and minimally invasive platform system and supports cross-modal neural interfaces to the cerebrum and other associated structures in the central nervous system. The neural interfaces comprise electrical and chemical interfaces for neural recording, electrical stimulation, chemical delivery, chemical sensing, chemical sampling, cell delivery, genetic material delivery and/or other functions of interest.

19 Claims, 4 Drawing Sheets

U.S. PATENT DOCUMENTS

| | | |
|---|---|---|
| 5,975,085 A | 11/1999 | Rise |
| 5,989,445 A | 11/1999 | Wise et al. |
| 5,992,769 A | 11/1999 | Wise et al. |
| 6,006,124 A | 12/1999 | Fischell et al. |
| 6,016,449 A | 1/2000 | Fischell et al. |
| 6,044,304 A | 3/2000 | Baudino |
| 6,181,569 B1 | 1/2001 | Chakravorty |
| 6,205,361 B1 | 3/2001 | Kuzma et al. |
| 6,228,111 B1 | 5/2001 | Tormala et al. |
| 6,324,433 B1 | 11/2001 | Errico |
| 6,374,143 B1 | 4/2002 | Berrang et al. |
| 6,430,443 B1 | 8/2002 | Karell |
| 6,600,231 B2 | 7/2003 | Tominaga |
| 6,618,623 B1 | 9/2003 | Pless et al. |
| 6,834,200 B2 | 12/2004 | Moxon et al. |
| 6,878,643 B2 | 4/2005 | Krulevitch et al. |
| 7,004,948 B1 | 2/2006 | Pianca et al. |
| 7,006,859 B1 | 2/2006 | Osorio et al. |
| 7,010,356 B2 | 3/2006 | Jog et al. |
| 7,011,680 B2 | 3/2006 | Alt |
| 7,089,059 B1 | 8/2006 | Pless |
| 7,548,775 B2 * | 6/2009 | Kipke et al. ............ 600/378 |
| 2002/0198446 A1 | 12/2002 | Hill et al. |
| 2003/0093129 A1 | 5/2003 | Nicolelis et al. |
| 2003/0100823 A1 | 5/2003 | Kipke et al. |
| 2004/0006264 A1 | 1/2004 | Mojarradi et al. |
| 2004/0102828 A1 | 5/2004 | Lowry et al. |
| 2004/0106169 A1 | 6/2004 | Evans |
| 2004/0199235 A1 | 10/2004 | Younis |
| 2005/0004627 A1 | 1/2005 | Gibson et al. |
| 2005/0021117 A1 | 1/2005 | He et al. |
| 2005/0137647 A1 | 6/2005 | Wallace et al. |
| 2006/0247749 A1 | 11/2006 | Colvin |
| 2006/0258951 A1 | 11/2006 | Bleich et al. |
| 2006/0276866 A1 | 12/2006 | McCreery |
| 2006/0282014 A1 | 12/2006 | Kipke et al. |
| 2007/0073130 A1 | 3/2007 | Finch et al. |
| 2007/0123765 A1 | 5/2007 | Hetke et al. |
| 2007/0135885 A1 | 6/2007 | Risi |
| 2008/0208283 A1 | 8/2008 | Vetter et al. |
| 2009/0102068 A1 | 4/2009 | Pellinen et al. |
| 2009/0118806 A1 | 5/2009 | Vetter et al. |
| 2009/0132042 A1 | 5/2009 | Hetke et al. |
| 2009/0187196 A1 | 7/2009 | Vetter |
| 2009/0234426 A1 | 9/2009 | Pellinen et al. |
| 2009/0240314 A1 | 9/2009 | Kong et al. |
| 2009/0248118 A1 | 10/2009 | Bradley et al. |
| 2009/0253977 A1 | 10/2009 | Kipke et al. |
| 2009/0299167 A1 | 12/2009 | Seymour |
| 2009/0312770 A1 | 12/2009 | Kozai et al. |
| 2010/0030298 A1 | 2/2010 | Martens et al. |
| 2010/0145422 A1 | 6/2010 | Seymour et al. |

FOREIGN PATENT DOCUMENTS

| | | |
|---|---|---|
| WO | WO-01/97906 A2 | 12/2001 |
| WO | WO-02/41666 A1 | 5/2002 |
| WO | WO-02/096482 A2 | 12/2002 |
| WO | WO-2008/038208 A2 | 4/2008 |
| WO | WO-2008/072125 A1 | 6/2008 |

OTHER PUBLICATIONS

PCT Notification of Transmittal of International Search Report (1 page).

Seymour, John P., Kipke, Daryl R. "Neural probe design for reduced tissue encapsulation in CNS" Biomaterials 28 (2007) 3594-3607, Apr. 5, 2007 (14 pages).

Seymour, John P., Elkasabi, Yaseen M., Chen, Hsien-Yeh, Lahann, Joerg, Kipke, Daryl R., "The insulation performance of reactive parylene films in implantable electronic devices" Biomaterials 30 (2009) 6158-6167, Aug. 22, 2009 (10 pages).

Kaplan, et al., "A Novel Fabrication Method of Capillary Tubes on Quartz for Chemical Analysis Applications" IEEE Proceedings, Micro Electro Mechanical Systems, pp. 63-68, Jan. 25-28, 1994 (6 pages).

Lin, et al., "Silicon Processed Microneedles"; IEEE Journal of Microelectromechanical Systems, vol. 8, No. 1, Mar. 1999, pp. 78-84. (7 pages).

* cited by examiner

INTRACRANIAL NEURAL INTERFACE SYSTEM

CROSS-REFERENCE TO RELATED APPLICATIONS

This application is a continuation of and claims benefit of U.S. patent application Ser. No. 10/970,268, filed Oct. 21, 2004, now U.S. Pat. No. 7,548,775, which claims priority based on U.S. Provisional Patent Application No. 60/513,035, filed Oct. 21, 2003, the entire contents of each application hereby incorporated into the present application by reference in full.

FIELD OF THE INVENTION

The present invention relates generally to systems, methods, and devices for interfacing with neurological systems.

BACKGROUND

Among researchers, clinicians and others, there is increasing interest in neural interfaces which may allow the transmission of information relating to neural activity, or delivery of therapeutic substances, to and from neurological systems. Some interfaces, such as cortical interfaces, show much promise for use in brain-machine interface systems, whether for purposes of accessing or delivery of chemical or biological substances or electrical signals, or for controlling or affecting machine or information system activities.

Implantable microelectrodes for such purposes have received increasing attention from interested persons, especially as biomaterials and the technology of microscale probes and electronics have improved. Thus, an unmet need remains for small scale neurological interfaces such as those comprising the present invention.

SUMMARY OF THE INVENTION

In some preferred embodiments, without limitation, the present invention comprises an implantable, intracranial neural interface node which is an integrated and minimally invasive platform system and supports cross-modal neural interfaces to the cerebrum and other associated structures in the central nervous system. The neural interfaces comprise electrical and chemical interfaces for neural recording, electrical stimulation, chemical delivery, chemical sensing, chemical sampling, cell delivery, genetic material delivery and/or other functions of interest.

In some preferred embodiments, without limitation, the invention is comprised of two or more elements, including an approximately cylindrical housing that is inserted into the cranium, one or more micro-scale neuroprobe assemblies that provide electrical and/or chemical interfaces to specific brain regions, one or more electronic components for instrumentation and signal conditioning, and/or one or more fluidic components for transmission of fluids, cells, gels, genetic material or other chemical or biological substances.

Other aspects of the invention will be apparent to those skilled in the art after reviewing the drawings and the detailed description below.

BRIEF DESCRIPTION OF THE DRAWINGS

The present invention will now be described, by way of example only, with reference to the accompanying drawings, in which.

Figure 1A:
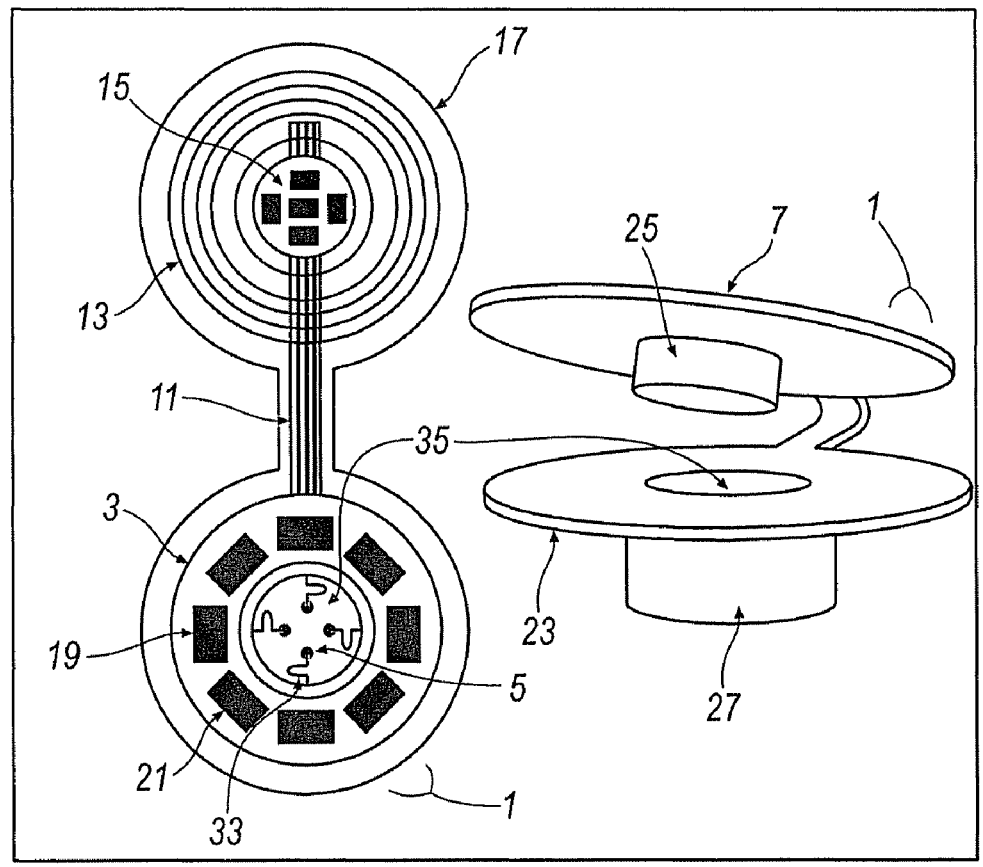
FIGS. 1(A)-(C) are respectively: (A) a three-dimensional schematic diagram of a cranial platform and layout of electronic subsystems within a skull base station; (B) a cut-away view of an inserted intracranial chamber; and (C) a view from within an inner lumen showing the protrusion of a neuroprobe assembly into the cortex.

Other aspects of the invention will be apparent to those skilled in the art after reviewing the detailed description below.

DETAILED DESCRIPTION

The invention comprises an integrated microsystem for creating a minimally invasive, microscale, multichannel neural interface for neural recording, stimulation, and/or delivery or uptake of drugs or other substances. In some preferred embodiments, without limitation, the intracranial neural interface node of the present invention comprises (i) an implantable intracranial chamber, optionally including a cover and/or a lumen plug, (ii) electronics and/or fluidic interface, as one example only, a rim circuit board, and (iii) neural interface electronics.

The intracranial chamber, or cranial platform, serves several functions in the invention. Among others, it provides a method to permanently occlude the cranial defect that results from the surgical burr hole and to seal the dura incision that results from exposing the cortical surface. It also provides a sealable package to house the electronics interface of the device. In addition, it provides a structure for packaging neuroprobe assemblies so that they can be reliably and efficiently manipulated and implanted by the neurosurgeon or other clinician in the operating room environment.

In some embodiments, the invention comprises a skull platform that utilizes the relatively generous dimensions afforded by the burr hole, the relatively thick skull, and the superior cranial surface surrounding the burr hole. The design or dimensions of the chamber or lumen is constrained by the neurosurgeon's need to visualize and manipulate the neuroprobe assemblies after the housing is located in the cranium.

The cross-modal interface system comprising the invention is capable of multiple modes of interaction with the brain and can interface with neural tissue on the spatial scale of nominally 1 micron to 1 cm. The invention comprises a device which interfaces with the brain with a high density of recording/stimulation sites in a target area of the brain, with appropriate system complexity to enable low-power embedded signal processing and wireless data transmission and a modular design that uncouples the neuroprobe design from the electronics interface and packaging designs, while allowing minimally-invasive access to the brain through the surgical burr hole in the skull.

In some preferred embodiments, the invention comprises a hollow intracranial chamber of approximately circular cross-section that is sized to fit in a surgical burrhole that is typical for accessing the human cerebral cortex. Such burr holes may be between 0.5 and 2.0 cm, although other sizes may also be used at times. In some embodiments, the top surface of the chamber is flush with the cranial surface, and the bottom surface extends part way through the cranium. The chamber may have a shelf for placement of the electronics interface. The chamber, and/or a corresponding lid, where desired, may be constructed from polysulfone, a machinable and biocompatible polymer, titanium, or other suitable plastic or metal material known to those of ordinary skill in the art.

Figure 1B:
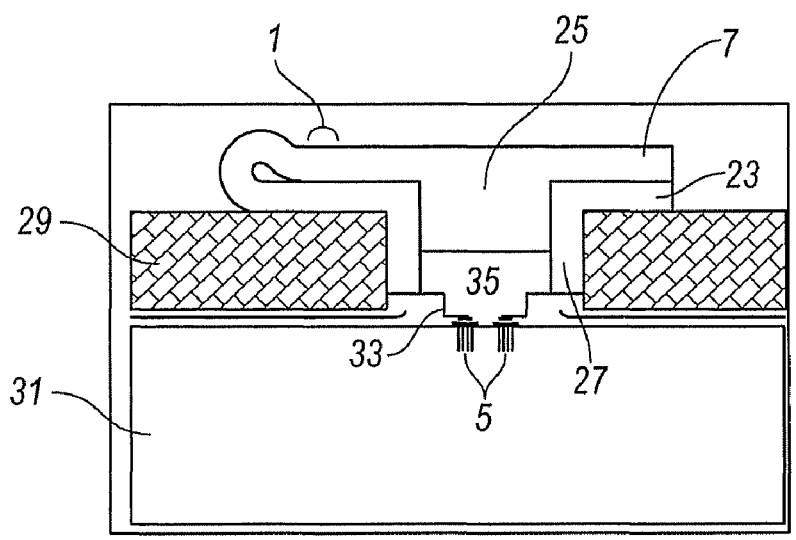
Figure 1C:
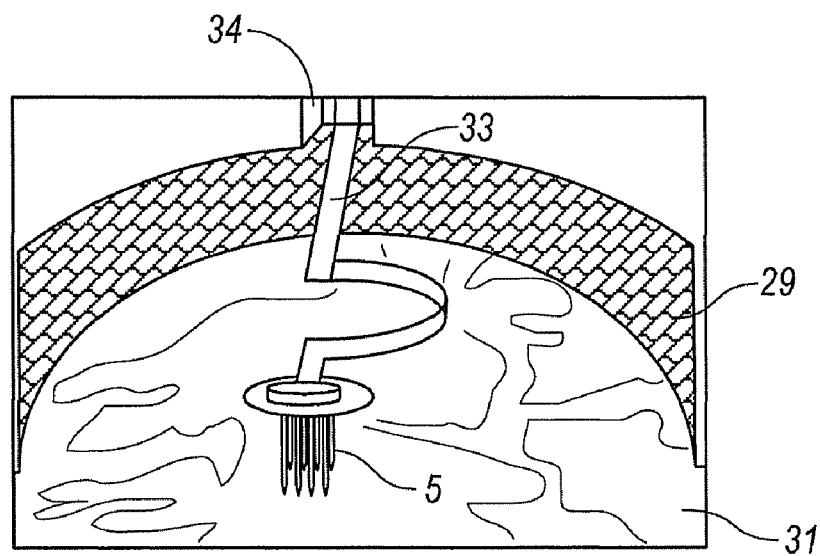

FIG. 1 shows one embodiment of a intracranial chamber or platform 1, without limitation. In this embodiment, the platform is comprised of two components, a top 7 and a skull plug component 27, that are machined from titanium and joined by a flexible multi-wire ribbon cable 11. The skull insert component 27 is milled from single stock to have an approximately 1.8 cm diameter cylindrical base with an open lumen 35 and a 2.5 cm diameter top flange 23. The flange is machined to have a recess on the top side that may house printed circuit boards 3. One or more grooves 34 (FIG. 1(C)) may be machined in the side walls of the inner lumen 35 to allow the passage of the flexible interconnect cable 33 from the bottom of the skull insert 27 to the printed circuit boards 3 at the top.

The top component 7 may also include a recess on its top to accommodate an RF coil 13 as well as a deeper recess in the center of the lumen plug 25 to house internal telemetry circuit components 15, where desired.

As illustrated in the embodiment of FIG. 1, the electrode 5 and flexible interconnect 33 subsystem attaches at the bottom of the base station plug 27, the signal conditioning subsystem electronics 19, 21 are located on the top of the base station platform 23, the telemetry electronics 15 reside in the lumen plug portion 25 of the base station top 7, and the RF coil 13 is embedded in the base station top 7.

Application-specific mixed-signal chips may be configured on a rim circuit board 3 that is machined to fit the annular structure of the skull insert. In some embodiments, without limitation, the invention may comprise one or more analog integrated circuits 19 for amplification, filtering, and/or multiplexing, and/or one or more digital integrated circuits 21 for data compression, signal feature detection, and/or telemetry.

The corresponding plug (FIG. 1) provides a conceptual layout illustrating multiple dies integrated onto a single circuit board. The circuit areas 3 on the top of the skull insert 27 and in the plug 7 are adequate for the chipset required for an intracortical interface node. This invention facilitates chip-level testing before the circuits and connectors are irreversibly sealed. The circuit boards for the two components may be connected with a flexible ribbon cable 11 to allow the plug to be folded and inserted into the lumen 35 of the skull insert during the intraoperative procedure without making new electrical or mechanical connections.

The intracranial chamber is inserted into a surgical burr hole in the cranium at a position roughly overlying the targeted neural structure. Without limiting the invention to a particular size or shape, the upper segment of the burr hole may have a larger diameter than the lower segment, with either a stepped or approximately tapered profile. The upper diameter may be in the range approximately 0.8 cm to approximately 2.5 cm and the lower diameter may be in the range of approximately 0.5 cm to approximately 2.3 cm. The transition between the two segments is in the range of approximately 0.3 cm to approximately 0.6 cm from the top surface of the cranium. The bottom surface of the device may be approximately flush with the bottom side of the cranium to provide access to the dura mater 31. The dura mater may be incised by the neurosurgeon to expose the surface of the cerebral cortex, although the dura membrane might not be incised for some applications. The upper surface of the device is approximately flush with the top surface of the cranium and may be shaped to follow the local contours of the cranium.

The housing material is comprised of one or more biocompatible polymers or metals. In some embodiments, without limitation, its outer surface is of a material and composition that promotes osseointegration to stabilize the housing in the cranium. The depth of the housing may be altered at the time of surgery to accommodate variable cranial thickness.

Figure 2:
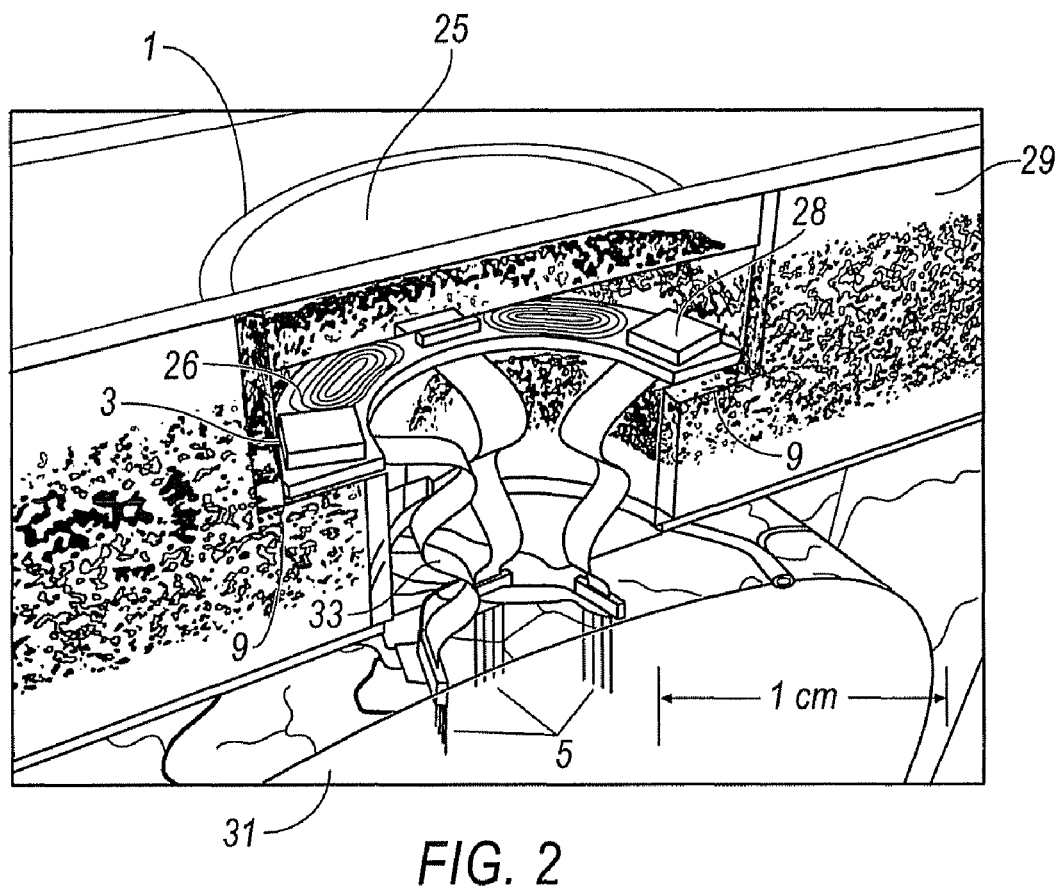
FIG. 2 is an illustration of one embodiment of the invention, without limitation.

FIG. 2 is an illustration of another embodiment of the invention, without limitation. In this embodiment, the invention comprises a hollow intracranial chamber 1 of approximately circular cross-section that is sized to fit in a surgical burrhole that is typical for accessing human cerebral cortex. The top surface of the chamber 1 is flush with the cranial surface, and the bottom surface extends part way through the cranium 29. The chamber may have a shelf 9 for placement of the electronics interface 3. The device may also have a lumen plug 25 that is threaded and screw fit to seal the device. The electronics interface comprises an interface board 3, as one example only, a printed-circuit board, which contains integrated circuits for signal conditioning and signal processing of the neural signals recorded by the implanted microelectrodes 5. The circuit may contain RF circuitry 26, as one example only, for inductive power, as well as application-specific circuitry 28. The neuroprobe assemblies comprise separate silicon microfabrication microelectrode arrays 5 that are individually manipulated and inserted into the brain and connected via interconnects 33 to the electronics interface 3. The site layout of the microelectrode arrays 5 is general in this illustration but may be optimized for use in particular regions of the brain. Each probe 5 is connected to the electronics interface 3 through a microfabricated interconnect cable 33.

In some embodiments, a segment of the chamber might extend to the top surface of the cranium. The walls of the chamber may not extend all the way to the lower surface of the cranium. The exterior walls of the chamber may also comprise a material to inhibit bone regrowth around the edge of the chamber. The upper and lower lumen sizes can vary (nominal range between 3 mm and 2.5 cm diameter). There might be wires and/or microcapillaries extending out of the chamber to additional devices or structures.

In some embodiments, the chamber includes a closely fit cover for the top surface. This cover might be screwed into the chamber or seated on a closely fit seals. It is intended to provide a hermetic seal of the chamber.

Figure 3:
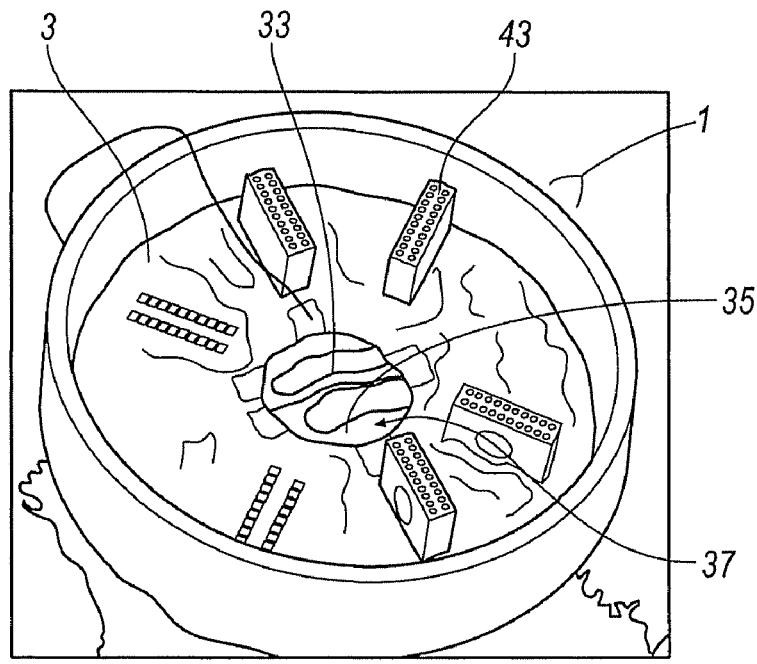
FIG. 3 is a photograph of one embodiment of the present invention, without limitation, with four silicon neuroprobes.

FIG. 3 is a photograph of one embodiment of the invention, without limitation to a single embodiment. This embodiment has silicon neuroprobes (not shown) with interconnects 33, shown here within the lumen 35 of the device. The electronics interface 3 has straight-through connectors 43 rather than integrated circuits. The circuit board is permanently attached to the intracranial chamber 1, with the top surface sealed and electrically insulated with epoxy (represented by gloss area over interface 3). The lumen 35 is filled with a hydrogel polymer 37.

In some embodiments, the invention comprises a lumen plug that is inserted into the lumen of the intracranial chamber to seal the brain compartment from the chamber compartment. The lumen plug may be comprised of a biocompatible polymer that accommodates and seals the interconnects that may extend between the brain compartment and chamber compartment. The plug may include both a plug material and a polymer sealant that is applied around its edges. In some embodiments, the plug may be of a material that cures or otherwise changes conformation due to ultraviolet light, heat, or other types of catalysts. It may also comprise a combination of soft and hard polymers.

In some embodiments, the lumen plug may comprise one or more components, as one example only and without limitation: (i) a biocompatible hydrogel, as one example only, an alginate, in contact with the brain and dura that eventually interacts with the tissue to form a hydrostatic seal between the brain compartment and the chamber compartment; (ii) a silicone elastomer or other suitable known to those of ordinary skill that fills all or a portion of the remaining volume of the lumen; and (iii) a lumen cover that forms a tight seal around the edge of the lumen, as some examples only, a polymethylmethacrolate or polysulfone cover or lid.

In some embodiments, without limitation, the invention comprises electronic and/or fluidic elements that may be located in the intracranial compartment to provide instrumentation, signal processing, and/or fluid processing functionality. The electronic elements may be placed on one or more printed circuit boards. In some embodiments, each board is flat and approximately circular with an open center to maintain the central lumen of the chamber. Multiple boards may be stacked in the chamber. The boards may be rigid or flexible. In other embodiments, one or more flexible circuit boards may be placed on the inner wall of the chamber. The bottom side of the lowest board may be seated on the chamber ledge. Optionally, a node may not have any active electronics in its electronics interface.

In some embodiments, without limitation, the invention may comprise one or more low-power chips to implement stages of on-board signal processing such as: (i) analog front-end electronics, (ii) real-time signal compression, and (iii) short-range telemetry. Such embodiments reflect a conservative and robust approach for implementing the requisite real-time neural signal processing. In some embodiments, the neural interface electronics are designed and/or selected to transmit the raw neural signals to an external, programmable real-time signal processor for analysis (e.g., for spike discrimination, neural feature extraction, and adaptive decoding). Embodiments of the invention comprise many of the advantages of on-board signal processing (e.g., amplification, site selection, wireless transmission) while also providing maximum flexibility in developing optimal algorithms to extract the relevant control information from the recorded spiketrains. At the same time, the invention comprises a solid platform that is adaptable to known and developing signal processing requirements of real-time cortical control in mammals.

In some embodiments, the neural interface electronics architecture of the invention may use a mixed-signal chipset at the user's choice. As some examples only, an analog integrated circuit ("IC") may provide amplification, filtering, analog/digital ("A/D") conversion, and front-end selection (multiplexing) for 32 channels of extracellular recordings. A digital IC implements spatial filtering, sub-band filtering, thresholding, and coding operations to provide real-time lossless signal compression. In some embodiments, a complete intracortical interface node having 128 sites may use four analog ICs and one digital IC. This implementation is advantageous because it allows the signal processing circuitry to be implemented with the smaller feature sizes and supply voltages of a modern digital circuit process; these digital processes are not compatible with the increased supply voltages and the high quality transistors that are required to implement reliable amplifiers and A/D converters (ADCs) appropriate for neural signal processing.

In some embodiments, the invention comprises a wireless communication channel for the intracortical interface node which (i) receives control data from an external control system, (ii) transmits compressed and digitized neural signals across the transcutaneous link, and (iii) supplies power to the implanted electronics. A telemetry receiver circuit may be included which is external to the subject, as one example only, packaged in a "Walkman-like" headband designed to position the receiver on the skin overlying the implanted transmitter coil.

In some preferred embodiments, without limitation, the invention comprises one or more neuroprobe assemblies comprised of one or more micro-scale devices that are inserted into or placed onto the brain to establish chemical and/or electrical interfaces to specific neural targets. Without limitation, some embodiments of the invention comprise the connection, integration and/or use of various combinations of these types of devices to result in a particular method to create an integrated cross-modal neural interface. The electrodes may be positioned on the surface of the brain, on the dura, or otherwise sited according to the user's choice. A combination of penetrating electrodes and surface electrodes may be used. The electrodes may be combined with one or more fluid delivery probes that either penetrate the brain or remain outside the parenchyma.

Some embodiments of the invention comprise the connection of multiple neuroprobe assemblies to an intracranial signal and fluidic processing node. In one embodiment, without limitation, an invention may include from 1 to 5 neuroprobe assemblies per node. Neuroprobes in some embodiments may be connected to the electronic and/or fluidic processing elements through flexible interconnects that transmit the appropriate electrical signals or fluidic channels.

In some embodiments, the neuroprobe assemblies are composed of silicon-substrate microelectrode arrays that are connected to the rim circuit board through flexible microfabricated ribbon cables, or interconnects. In some embodiments, a device comprising the invention may contain 4 to 6 separate 32-channel neuroprobe assemblies that are regularly positioned around the lumen of an annular rim circuit board, which may have a nominal lumen diameter in some embodiments of 0.5 to 2 cm.

The invention comprises more system complexity in a smaller package or "footprint" than any existing device, with packaging and bonding such that separate microelectrode arrays can be individually placed within a small volume of the brain. The use of the intracranial chamber for housing system components reduce the level of invasiveness. The use of an annular circuit board in some embodiments provides a central access to the brain surface, while retaining system complexity and low-footprint device. Moreover, bonding the multicontact probes to the interface board reduces the lead complexity to enable high-channel count systems. The invention also allows direct visualization of the insertion of the probes by the surgeon or clinician in order to avoid surface vasculature.

Figure 4:
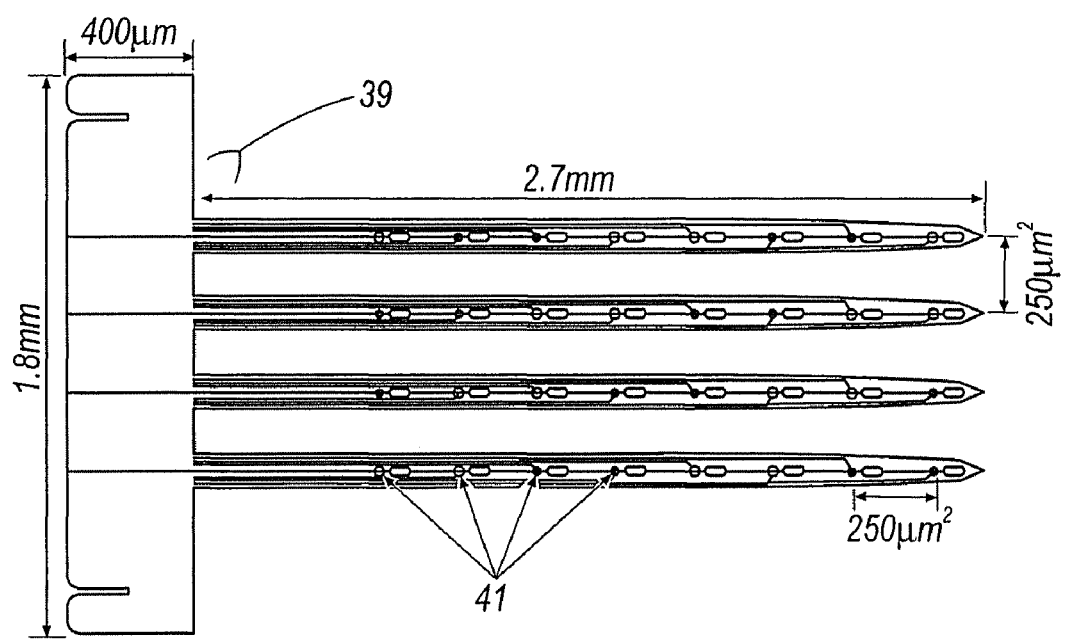
FIG. 4 is a layout of a microelectrode in accordance with one embodiment, without limitation.

In some embodiments, the silicon microelectrode of choice is a 32-channel device with four penetrating shanks (FIG. 4), with design features selected based on published human anatomical data. FIG. 4 is layout of a microelectrode 39 in accordance with one embodiment, without limitation. The shanks of this embodiment are 25 millimeters×107 millimeters in cross-section and terminate in a relatively sharp tip. A variety of different site areas 41, ranging from 200 to 1000 $\mu m^2$, may be included to affect recording quality as it relates to site area. The tip shape is based on successful insertion tests in fresh human cadaver brain. Typical penetrating shanks have cross-section dimensions of 15×60 microns and length of the penetrating shank of 2-3 mm.

In some embodiments, the invention may comprise one or more so-called "Michigan probes," a particular type of microfabricated silicon substrate microelectrode known to those of skill in the art. See e.g., Hetke, et al., "Silicon microelectrodes for extracellular recording" in W. E. Finn (ed.), *Handbook of*

*Neuroprosthetic Methods* (Boca Raton, Fla.: CRC 2002). This probe has several favorable attributes including batch fabrication, reproducibility of geometrical and electrical characteristics, easy customization of recording site placement and substrate shape, small size, and the ability to integrate it with a silicon ribbon cable and to include on-chip electronics for signal conditioning. The extensibility of the platform technology also enables custom designs for diverse applications. For example, planar probes have been assembled into multiplanar arrays for precise three-dimensional placement of recording sites in the brain, and the probes have been combined with a polymer ribbon cable to form a hybrid assembly to provide additional mechanical flexibility. Probe designs include microchannels along the shanks for microscale and controlled fluid delivery through the blood brain barrier. These silicon probes are currently used by many investigators and are now well validated for recording both spike activity and field potentials in diverse brain structures over acute and semichronic time durations up to several weeks. The probes have been found reliable for recording multichannel spike activity and local field potentials over studied time periods, thus demonstrating the feasibility of using the probe in an implantable microscale chronic intracortical neural interface for medical applications, including cortical prostheses, like those comprising the present invention. In some embodiments, without limitation, the microelectrode of choice is a polymer-substrate microelectrode of a type described in P. J. Rousche, D. S. Pellinen, D. P. Pivin, Jr., J. C. Williams, R. J. Vetter, and D. R. Kipke, "Flexible polyimide-based intracortical electrode arrays with bioactive capability," *IEEE Trans Biomed Eng*, vol. 48, pp. 361-71 (2001).

Figure 5:
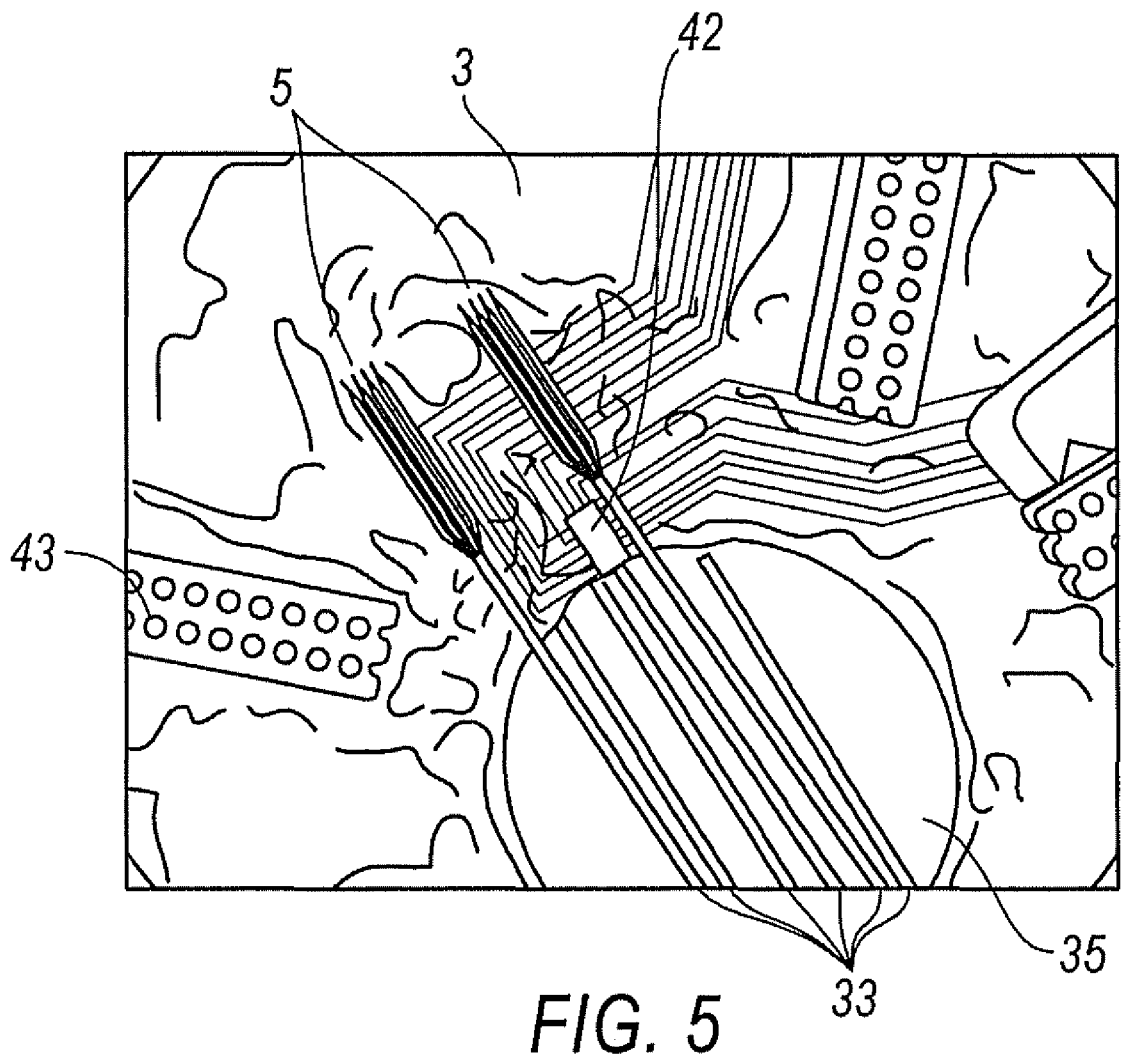
FIG. 5 shows a detailed view of a connection between the silicon neuroprobes and the printed circuit board of an electronics interface of one embodiment, without limitation.

FIG. 5 shows a detailed view of a connection between the silicon neuroprobes and a printed circuit board 3 of an electronics interface of one embodiment, without limitation. In this view, the device has not yet been placed in situ. Two of six 4-shank probes 5 can be seen in the top-left region of the view are attached to the board at their other end (out of view). Interconnects 33 for the probes are also shown in part in the lumen 35, with the shinier colored interconnects 33 leading to probes folded on top of the device before placement, and the darker colored interconnects attaching to probes (not shown) folded underneath the plane of the circuit board 3. A bond-pad region 42 of a separate probe is seen at the center of the photo. The individual traces of the probe are attached to the board using wirebonds and then sealed with epoxy (represented by gloss areas on circuit board 3).

The interconnects provide mechanical, electrical, and/or fluidic connections between the probe assembly and the rim circuit board. The interconnects may be flexible in order to minimize tethering forces on the brain, comparable in size to the scale of the probe assembly, and mechanically robust to withstand surgical manipulation. As one example only, one type of interconnect comprising the invention is a silicon ribbon cable which can be integrated directly with the back end of the probe. Choice of the interconnect design can also improve mechanical stability. For example, meandering (i.e. zigzagging) and microfabrication with silicon or polymer and slotting of the cables may improve resistance to breakage during twisting and in-plane bending, flexibility, and strain relief.

An alternative interconnect is a microfabricated polymer ribbon cable. Polyimide is a desirable cable substrate due to its flexibility, process compatibility, mechanical robustness, and biocompatibility. The polymer cables can be constructed of alternative polymers such as parylene or liquid crystal polymer. Additional insulation to the polyimide cables may be added with an underlying layer of silicon dioxide and a top layer of silicone. Liquid silicone rubber may be spun on (or possibly deposited using PECVD) and cured and either dry-etched and/or laser ablated to open contacts and clear the field regions. A backside etch may be performed in hot 20% KOH to dissolve the silicon wafer carrier and the devices removed from their frame using a laser. The design of the polyimide cables may be adapted by slitting in between the metal leads, permitting silicone to flow between them and consequently inhibit leakage between leads.

In some embodiments, without limitation, the probe assembly and interconnect may be fabricated of similar materials so that they are integrated and no separate connector is required.

In some embodiments, without limitation, the invention comprises one or more integrated fluidic elements in the chamber in order to manipulate and control fluid delivery and/or sampling to the neuroprobes. These elements may be integrated in or placed on separate boards in the chamber. Alternatively they may be attached to the intracranial chamber. These elements may include, without limitation, valves, flow meters, pumps, pressure sensors, optical sensors, and reservoirs. Some of these elements may be controlled with electrical signals. The electronics and fluidic interface may be located in the intracranial space or on the surface of the cranium. The electronics interface board may be integrated with flexible interconnects (leads) to the neuroprobes. The interface may contain a combination of active electronic components. The interface board may contain fluid control components, such as valves and/or pumps. The interface board may not be uniformly planar (flat), having vertical, slanted, or curved components. The electronic interface might involve a microprocessor for signal processing, including data compression or feature coding.

The invention provides a minimally invasive neurosurgical method for creating a chronic neural interface that has the system complexity for advanced therapies, as one example only, for recording from a plurality of sites. It invention comprises a modular and scalable architecture that can be used to establish short-term or chronic neural interfaces for neural recording, electrical stimulation, or microscale drug delivery. As some examples only, embodiments of the invention may be used to acquire control signals in a cortical prosthetic system, for cortical microstimulation for treatment of pain, and for localized drug delivery to brain tumors for chemotherapy.

This invention comprises the first known, fully implantable, cross-modal device for chronically recording from neurons in the nervous system. It is a fully implantable device, without any transcutaneous components, and allows for multiple modes of operation (electrical recording, stimulation, chemical delivery, chemical sensing, stem cell delivery, gene delivery, etc). It is minimally invasive and replaceable if the unit is damaged or fails.

In practice, the clinician may use more than one intracranial interface node per patient. Multiple nodes may be connected either physically or through wireless telemetry. A node might be connected to one or more external devices or implanted devices elsewhere on the body through physical or wireless connections. A node might include sensors of other physiological signals, such as electrocardiogram.

For a number of medical applications, one may wish to implant nodes in each hemisphere. For example, in cortical neuroprostheses it would be beneficial to record/acquire signals from motor cortex in each hemisphere of the brain. Another example, for deep-brain stimulation ("DBS"), it would be useful to use a node to record in motor cortex to provide feedback for neurostimulation. In this case, the DBS electrode would be implanted through a separate burr hole. In both of these cases, the recording nodes would connect with either external or implanted microprocessors.

EXAMPLE

A probe was populated with six 16-ch. 4 mm 200 chron probes (1250 um$^2$ sites). A 10 mm trephine was used to create a craniotomy in the test subject, a monkey. The dura was completely removed exposing the brain throughout the entire craniotomy. After removal of the dura, a layer of agar was administered over the cortex via syringe, which filled the entire craniotomy. The agar thickness was approximately 3 mm. A thin layer of Kwik-Sil (elastomer polymer, WPI) was applied around the perimeter of the craniotomy prior to placement of the interface. This aided in sealing off the brain from the external environment. The interface was positioned over the craniotomy, with the inner lumen of the interface resting on top of the agar. It was cemented into place with dental acrylic and the ground wire was attached to two bone screws. The probes were implanted one at a time through the agar into the cortex. Once all six probes were inserted, the inner lumen was filled with Kwik-Sil such that the entire ribbon cable of each probe was encapsulated with the polymer. Dental acrylic was applied over the Kwik-Sil to provide protective rigid coatings. Results showed that neural recordings were present in all recording arrays (16-ch. Arrays) which penetrated the agar 24 hours post-implant. It was determined that the average impedance on the electrodes showing unit activity were approximately 400 kohms (measured with a system using a 1 kHz signal, manufactured by BAK).

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements. Each of the references identified herein is hereby incorporated by reference as though fully set forth herein.

The invention claimed is:

1. An implantable neural interface node, comprising:
a base insertable into a mammalian cranium;
a plurality of neuroprobe assemblies coupled to the base;
an electronic component coupled to at least one of the neuroprobe assemblies, wherein the electronic component includes a power source; and
a plug coupled to the base; wherein the plug includes a recess on a side of the plug;
wherein the recess on the side of the plug houses at least a portion of the electronic component.

2. The implantable neural interface node of claim 1, wherein the power source is an inductive power source.

3. The implantable neural interface node of claim 2, wherein the inductive power source is an RF coil.

4. The implantable neural interface node of claim 1, wherein at least one of the neuroprobe assemblies includes a microelectrode array.

5. The implantable neural interface node of claim 4, wherein the microelectrode array includes at least one shank that is equal to or less than 3 millimeters in length.

6. The implantable neural interface node of claim 4, wherein the power source is an inductive power source.

7. The implantable neural interface node of claim 6, wherein the inductive power source is an RF coil.

8. An implantable neural interface node, comprising:
a base insertable into a mammalian cranium;
a plurality of neuroprobe assemblies coupled to the base; and
an electronic component coupled to at least one of the neuroprobe assemblies, wherein the electronic component includes a power source,
wherein the base includes a shelf and the electronic component includes a circuit board on the shelf within the base;
wherein the circuit board is substantially flat and circular and defines an open center.

9. An implantable neural interface node, comprising:
a base insertable into a mammalian cranium, wherein the base includes a groove from a bottom portion of the base to a top portion of the base;
a plurality of neuroprobe assemblies coupled to the base;
an electronic component coupled to at least one of the neuroprobe assemblies, wherein the electronic component includes a power source; and
a flexible interconnect cable that connects the electronic component to at least one neuroprobe assembly; wherein a least a portion of the flexible interconnect cable resides in the groove.

10. The implantable neural interface node of claim 9, wherein at least one of the neuroprobe assemblies includes a microelectrode array.

11. The implantable neural interface node of claim 10, wherein the microelectrode array includes at least one shank that is equal to or less than 3 millimeters in length.

12. The implantable neural interface node of claim 9, wherein at least one of the neuroprobe assemblies includes a fluidic component.

13. An implantable neural interface node, comprising:
a base insertable into a mammalian cranium;
a plurality of neuroprobe assemblies coupled to the base; wherein at least one of the neuroprobe assemblies includes a micro-scale neural target interface device;
an electronic component coupled to at least one of the neuroprobe assemblies; and
a plug that couples to the base; wherein the plug includes a recess on a side of the plug; wherein the recess houses at least a portion of the electronic component.

14. The implantable neural interface node of claim 13, wherein the micro-scale neural target interface device includes a microelectrode array.

15. The implantable neural interface node of claim 14, wherein the microelectrode array includes at least one shank that is equal to or less than 3 millimeters in length.

16. The implantable neural interface node of claim 14, wherein the micro-scale neural target interface device also includes a fluidic component.

17. The implantable neural interface node of claim 13, wherein the electronic component includes a power source.

18. The implantable neural interface node of claim 17, wherein the power source is an inductive power source.

19. The implantable neural interface node of claim 13, wherein the electronic component includes a wireless communication channel.

* * * * *